(12) United States Patent
Epstein

(10) Patent No.: US 6,951,556 B2
(45) Date of Patent: Oct. 4, 2005

(54) METHOD AND APPARATUS FOR CORRECTING OFF-CENTER LASER ABLATIONS IN REFRACTIVE SURGERY

(76) Inventor: Robert L. Epstein, 5400 W. Elm St., McHenry, IL (US) 60050

( * ) Notice: Subject to any disclaimer, the term of this patent is extended or adjusted under 35 U.S.C. 154(b) by 265 days.

(21) Appl. No.: 10/188,694

(22) Filed: Jul. 1, 2002

(65) Prior Publication Data

US 2004/0002696 A1 Jan. 1, 2004

(51) Int. Cl.⁷ .................................................. A61F 9/01
(52) U.S. Cl. .............................. 606/5; 606/10; 129/898
(58) Field of Search ............................... 606/5, 10–13; 128/898

(56) References Cited

U.S. PATENT DOCUMENTS

| | | | |
|---|---|---|---|
| 5,284,477 A | 2/1994 | Hanna et al. | |
| 5,613,965 A | 3/1997 | Muller | |
| 5,634,919 A * | 6/1997 | Azar | 606/5 |
| 5,683,379 A | 11/1997 | Hohla | |
| 6,063,072 A | 5/2000 | Muller | |
| 6,099,541 A | 8/2000 | Klopotek | |
| 6,293,938 B1 | 9/2001 | Muller et al. | |
| 6,331,177 B1 | 12/2001 | Munnerlyn et al. | |

OTHER PUBLICATIONS

Talamo et al "Management of Ablation Decentration Following Excimer Photorefractive Keratectomy" Arch Ophthalmol. vol. 113 Jun. 1995 pp. 706-707.*

* cited by examiner

Primary Examiner—David M. Shay
(74) Attorney, Agent, or Firm—George H. Gerstman; Seyfarth Shaw LLP

(57) ABSTRACT

A novel method and apparatus are provided for correcting an off-center laser ablation in the cornea, in which the original ablated area has a center that is offset from the correct center of the optical cornea. The method comprises the steps of determining the correct optical center of the cornea and the offset location of the ablation; performing a supplemental laser ablation on the cornea with the laser beam covering generally the original ablated area, and with the energy of the supplemental laser increasing in a direction from the offset center toward the correct center; introducing a laser shield to cover the entire original ablated area; and performing another laser ablation with the correct optical center as the center of the ablated area.

18 Claims, 4 Drawing Sheets

METHOD AND APPARATUS FOR CORRECTING OFF-CENTER LASER ABLATIONS IN REFRACTIVE SURGERY

FIELD OF THE INVENTION

The present invention concerns a novel method and apparatus for correcting an off-center laser ablation in the cornea.

BACKGROUND OF THE INVENTION

Corneal refractive surgery, done for the purpose of reducing or eliminating the visual dependence on eyeglasses and contact lenses, started in 1978 in the U.S. with the first radial keratotomy procedures by Bores, who learned these procedures from Fyodorov of Moscow, Russia. Both Bores and Fyodorov taught radial keratotomy to many U.S. eye surgeons.

With the increasing use of corneal refractive surgery in the 1980s, a few surgeons added keratomileusis, a procedure originated by Barraquer of Bogota, Colombia, to their surgical armamentarium. Keratomileusis involves removing a contact lens shaped piece of the front of the human cornea, changing its curvature by freezing and lathing the inside of the removed tissue using a device called a cryolathe, and then suturing the corneal cap back onto the eye. Cryolathe keratomileusis was successful in eliminating eyeglass dependency in cases too extreme for the use of radial keratotomy but the freezing of the tissue was associated with a prolonged healing time.

During the late 1980s and early 1990s, Ruiz modified keratomileusis to eliminate the freezing step. The microkeratome was first used to cut a cap of tissue off the cornea as in the cryolathe keratomileusis. Then instead of modifying the resected corneal cap, a second incision of a small amount of tissue from the remaining eye tissue was used to produce optical correction. The cap was then replaced. Healing of the exterior of the eye was faster and more comfortable than in cryolathe keratomileusis. In the mid 1980s and again in the early 1990s, Ruiz modified the first step of his procedure by producing a flap with a nasal hinge rather than a cap. Ruiz's procedure was named automated lamellar keratoplasty. Although the healing was more rapid than cryolathe keratomileusis, the use of the second microkeratome to remove a very thin silver to change eye optics was flawed. It was difficult to produce second cuts to produce accurate enough optics and there were problems with contamination of outer covering cells being deposited under the repositioned corneal cap or flap.

By the early to mid 1990s, the excimer laser, a device initially to cut electronic circuit boards, had been modified by Trokel and others to remove the tissue directly from the eye to modify the eye curvature. At first the excimer laser was developed to make radial keratotomy incisions, but this failed. Then, the excimer was used to directly modify the corneal surface in a procedure called photorefractive keratoplasty or PRK. This procedure is used to the present day but is characterized by pain during early healing and a three-month period of full return of vision.

The excimer laser brought the ability to more precisely determine the center of the optical cut, but there was and is to this day, some debate as to where is the proper place to center the optical cut with the excimer laser. Some surgeons argue for placement over the center of the pupil and some for placement over the true optical center. This debate leads some surgeons to compromise and place the center of the optical cut somewhere between the center of the pupil and the true optical center of the eye. Certainly some patients have had excimer laser treatments where the optical center of treatment has been placed incorrectly.

Barraquer in 1984 proposed the "laser lathe" to replace the cryolathe step on the resected cap in cryolathe keratomileusis but he did not produce an instrument or do this surgery. Peyman proposed doing a microkeratome resection of the cornea and then placing the excimer ablation directly on the cornea beneath the resected tissue and then replacing the resected cap. He did not do this surgery, but outside the U.S., Burratto performed the first such procedure in 1990. Maloney, Epstein, and Brint separately performed the first intrastromal laser keratomileusis procedures in the United States in 1991. The name Lasik for Laser In Situ Keratomileusis (or Laser Intrastromal Keratomileusis) was given to the procedure.

In the present day, LASIK is performed by first using a microkeratome to produce a nasally hinged flap (or occasionally an unhinged cap) and then applying shaping excimer laser treatment to the eye tissue remaining after the resected tissue is moved out of the way. LASIK resembles Barraquer's keratomileusis and Ruiz's automated lamellar keratoplasty, but the excimer laser produces the tissue removal to change optics.

The Optical Centers, The Cornea and Vision

In all the corneal refractive surgeries mentioned, the treatment of myopia is the flattening of the central part of the human cornea. For each eye there is an optical center of the cornea. The optical center of the cornea is the projection of the visual axis on the cornea. The visual axis is that straight line that goes between the point of regard (such as a distant star) and the person's fovea. The optical center does not necessarily correspond to the geometric center of the cornea and is not necessarily in line with the center of the pupil.

Corneal topographic mapping is customary in the preoperative examination of a patient for refractive surgery, in particular for LASIK. Corneal topographic mapping is a common examination after corneal refractive surgery, especially in cases where vision is not satisfactory to the patient. Modern corneal topographic instruments can produce maps both of the curvature at different points on the cornea but also a map of the elevation of the cornea with respect to that of a best fitting perfect sphere.

After LASIK treatment, subtraction maps can be taken to determine where the excimer treatment actually occurred with respect to the true optical center of the cornea. When LASIK treatment is directed at the optical center of the cornea, then corneal topography elevation subtraction mapping shows a circle of color change corresponding to an elevation change which is centered on the elevation graph. Many surgeons have observed that when PRK or LASIK is performed where the laser-induced changes of the cornea do not correspond with the optical center of the cornea, there can be a blurring of vision or other various aberrations of vision. In other words, "off-center" ablations are associated with blurring of vision. The blurring of vision due to an irregular shape of the cornea is called "irregular astigmatism" and often cannot be corrected with spectacles and may only be correctable with hard contact lenses. Since people elect to have corneal refractive surgery because of the inability or dislike of wearing contact lenses, irregular astigmatism can be visually disabling.

Why Excimer Ablations Can Be Off-Center

Excimer laser ablations can be off center for various reasons: If the excimer laser contains a system to identify the edge of the pupil as the anchor for the position of the laser beam, then there are problems. There are problems because the center of the pupil is not necessarily in the center of the line of sight. Even if the center of the pupil were coincident with the line of sight, there can be problems. Since the pupil is located in a plane behind the plane of the cornea, it is possible for the optical center of the cornea to move out of the line of sight during a laser treatment if the eye is turned. If the laser beam is aligned with the pupil and not the cornea, then the treatment can smear over the cornea and produce an irregular result. Such turning of the cornea could easily happen. The patient cannot be relied upon to move the eye into the proper position. The patient may have poor vision without glasses. During a LASIK procedure, the cornea has been cut and so the patient's vision at the moment of excimer laser treatment is drastically reduced. Also, the patient is nervous and may not follow directions at the dramatic moment that the laser treatment is applied.

It is an object of the present invention to provide a method and apparatus for moving the optical center of an already accomplished excimer ablation to become on center.

Another option of the present invention is to provide a corrective laser ablation which is relatively simple in operation.

Other objects and advantages of the present invention will become apparent as the description proceeds.

SUMMARY OF THE INVENTION

In accordance with the present invention, a method is provided for correcting an off-center laser ablation in the cornea, in which the original ablated area has a center that is offset from the correct optical center of the optical cornea. The method comprises the steps of determining the correct optical center of the cornea and the offset location of the ablation; and performing a supplemental laser ablation on the cornea with the total energy per square millimeter of the supplemental laser increasing in a direction defined by a vector originating from the offset center and pointing toward the correct center.

In one embodiment, the method includes the steps of introducing a laser shield to cover the entire original ablated area; and performing another laser ablation with the correct optical center as the center of the ablated area.

In one embodiment, the other laser ablation covers an area of a disc having a diameter substantially equal to the diameter of the initial ablation plus twice the distance to which the original ablation was off center.

In one embodiment, the energy of the supplemental laser increases at a uniform rate and the supplemental laser ablation step includes the step of providing a laser masking device which moves in a direction defined by a vector from the offset center toward the correct center.

The supplemental laser ablation step in another form of the invention includes the step of providing a laser masking device having a laser-energy penetrability that varies from less penetrable to more penetrable in a direction from the offset center toward the correct center. The result is a correcting laser ablation that is deeper on one side of the eye than on the other side.

In one embodiment, the masking device is totally impenetrable and moves at a controlled uniform speed with the speed of the masking device being inversely proportional to the product of the distance of the offset center from the correct optical center times the number of diopters of optical correction that were placed in the original ablation. The laser masking device has a straight edge and the supplemental laser ablation uses a pulsing, uniform-energy circular disc-shaped laser beam.

The present invention also concerns an apparatus for correcting an off-center laser ablation in the cornea, in which the original ablated area has a center that is offset from the correct optical center of the cornea, and in which a corneal topographic instrument is used to determine the vector between the offset center of the ablation and the correct optical center.

In one embodiment, the apparatus comprises a laser for performing a supplemental laser ablation on the cornea with the total energy per area of the supplemental laser increasing (in particular in a linear manner) in a direction defined by a vector from the offset center toward the correct center.

In one embodiment, the apparatus comprises a movable laser masking device for use in performing a supplemental laser ablation on the cornea. The laser masking device is movable in a direction from the offset center toward the correct center to enable supplemental laser energy to increase in the direction from the offset center toward the correct center. A laser shield is provided for covering the entire original ablated area to enable another laser ablation to be performed without ablating the original ablated area.

In accordance with the present invention, a method and apparatus are provided to repair visual loss from off center excimer ablations. The method and apparatus shape a subsequent repairing excimer ablation so that the combined excimer ablation, that is the damaging one plus the repairing one, is properly centered and produces a uniform optical correction.

One form of the invention utilizes a movable laser masking device resembling a closing garage door. The masking device is designed to move over a uniform energy excimer ablation so that one side of the eye receives more ablation than the other side. In the preferred form, the masking device moves at a controlled uniform speed in a direction defined by a vector originating from the center of the damaging laser ablation and pointed in the direction of a point that is the true optical center of the eye as projected onto the cornea. The speed of the masking device is inversely proportional to the product of how far off center was the damaging ablation times the number of diopters of optical correction that were placed in the initial excimer ablation.

A more detailed explanation is provided in the following description and claims and is illustrated in the accompanying drawings.

DETAILED DESCRIPTION OF THE ILLUSTRATIVE EMBODIMENTS

Figure 1:
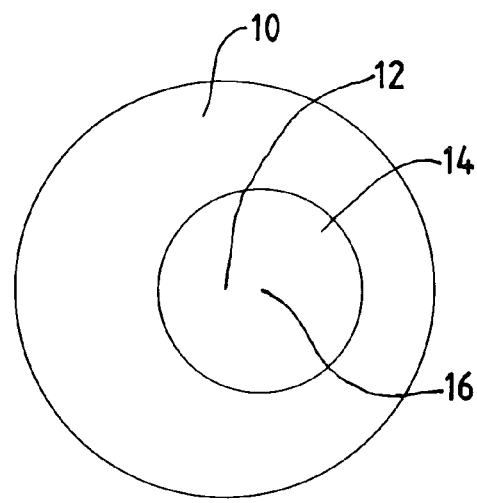
FIG. 1 is a diagrammatic view of the cornea of an eye with a representation of an off-center laser ablation.
Figure 2:
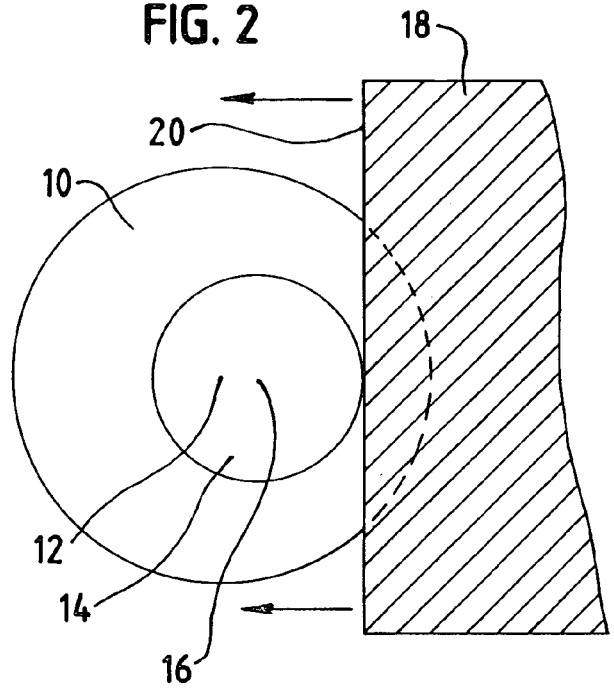
FIG. 2 is a diagrammatic view thereof, with a laser masking device diagrammatically shown at the beginning of the first phase of a correcting method in accordance with the present invention.
Figure 3:
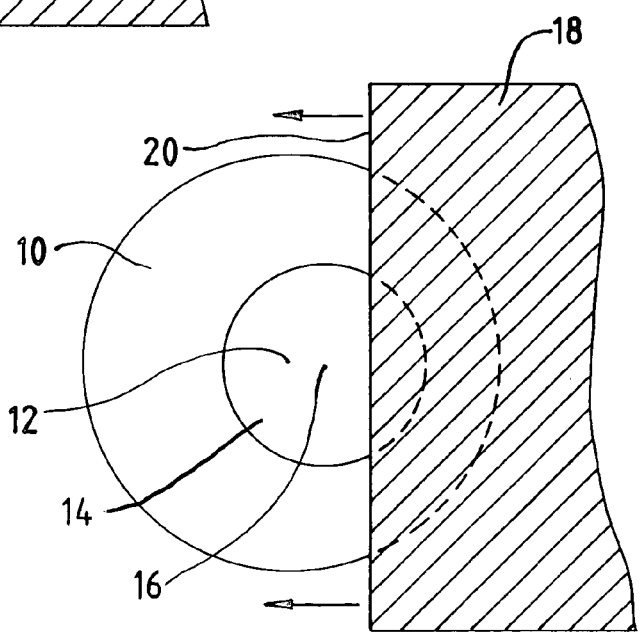
FIGS. 3–5 are diagrammatic views thereof, showing the laser masking device at increasingly later times during the first phase of the correcting method.
Figure 4:
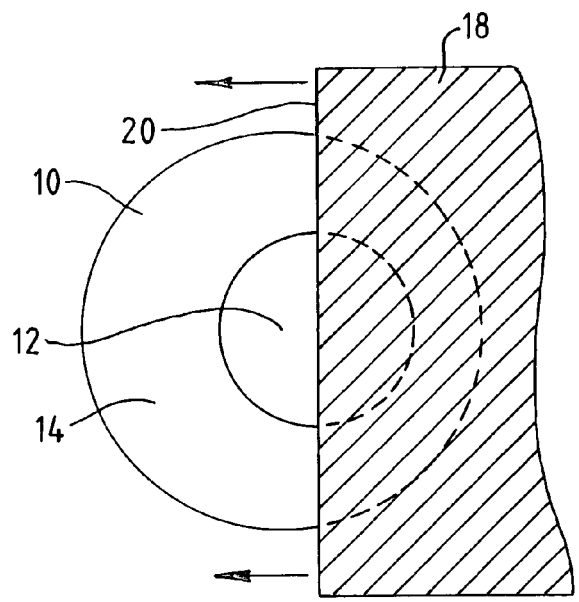
Figure 5:
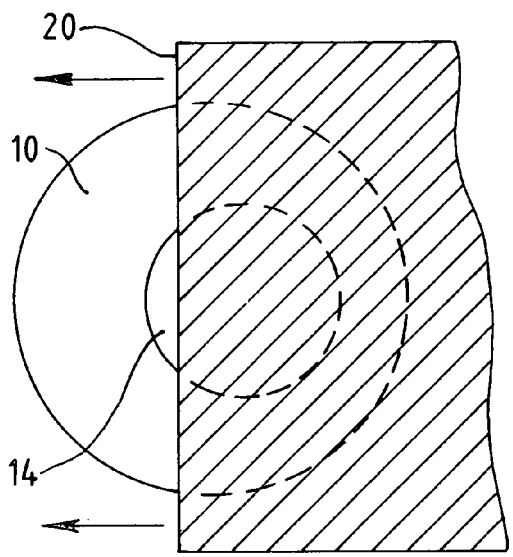

Creating Laser ablations Properly Centered Over the Optical Center of the Cornea The key to creating a properly centered laser ablation is the proper marking of the cornea itself because it is on the cornea itself that the laser treatment is done. It is important for the marking to be readily visible when the surgeon views the treatment surface on the inside the cornea during the laser treatment.

Prior to excimer laser treatment, the cornea and conjunctiva are well anesthetized with standard agents. A microscope is equipped with a light source which produces a tiny red light which is coaxial with the right eye ocular of the surgeon. The patient is directed to look at the fixation light and using a special tiny marker designed by this surgeon, Katena K3-8102, the surgeon sights through the right ocular and places a single mark on the patient's cornea as close as possible centered over the reflection of the red light back into the right ocular.

Then using another fine instrument, such as the end of a Sinsky hook, the surgeon transfers a few microliters of 10% fluorescein gently over the mark just made on the patient's cornea. No new marks are made and the patient's eye remains open for thirty seconds while the fluorescein soaks through the mark into the stroma of the patient's cornea. The patient then blinks ten times to remove the fluorescein and the surgeon places a drop of artificial tears over the cornea. The surgeon then immediately sights onto the patient's cornea to observe the reflection of the red dot into the surgeon's right ocular and now also the green dot from the surgeon's marking. The reflection of the red dot corresponds to the patient's true optical center and the center as measured by corneal topography. The surgeon then draws a map that shows placement of the green dot as it relates to the placement of the red light reflection on a small piece of paper.

After other marks for axis and for replacement of the cornea after creation of the keratectomy flap are made, a microkeratome is used to make the corneal flap. The patient's operative eye is aligned under the excimer laser. The corneal flap is raised for the application of the excimer laser. The green fluorescein mark shows on the stroma below the lifted corneal flap. A cobalt blue light is shined on the operative surface to accentuate the green of the corneal stromal mark and no other lighting on the microscope is used other than the ambient room lights. The laser is aimed so as to be on the exact spot corresponding to the optical center of the cornea as approximated and mapped with respect to the green fluorescein dot previously mentioned.

Discovering An Off-Center Ablation

When on-center excimer laser ablations have been created, then the commonly available corneal topographic mapping machines will show that the ablation is properly centered. To prove than an excimer laser ablation is on the optical center, one must have corneal topography prior to treatment and after laser treatment. Performing corneal elevation topography is particularly helpful. Most elevation topography machines have the capability of producing subtraction maps in which the relative elevation of the cornea after ablation is subtracted from that occurring before ablation. A color coded map typically shows relative elevation in colors toward the red end of the spectrum and relative depressions in colors toward the purple end of the spectrum. The corneal topography device maps the elevation of the cornea with respect to the optical center of the cornea and the coordinates are general radial, i.e. distance from center in degrees. The subtraction map of a cornea that has had excimer laser ablation for myopia shows a typically circular region of depression that is centered about the optical center of the cornea. The depressed area is relatively more purple or blue than the surrounding areas.

By doing a subtraction elevation corneal topography mapping, it is possible to see that an ablation is off center and one can visually determine the actual center of the excimer ablation relative to the true center.

The Present Invention

A patient may have been treated for myopia with an excimer laser ablation that is good in all respects except that it was placed off-center. If vision is impaired, corneal topography should be taken. A subtraction corneal topography comparing postoperative and preoperative corneal elevation mapping can demonstrate the direction and distance off optical center of the location of the excimer laser ablation.

The present invention concerns a method of moving the optical center of the excimer ablation to become on-center and includes apparatus to move the optical center of the ablation.

In summary, the method of treating the off-center ablation entails providing another laser ablation over the same area and beyond the bounds of the original ablation.

Referring to FIG. 1, a cornea 10 is shown therein with a correct optical center 12 and an off-center original ablated area 14 having an offset center 16. Thus correct center 12 is the true optical center of the eye and off-center 16 is the center of the wrongly-centered laser ablation. It is to be understood that the drawings are for illustrative purposes and are not necessarily to scale.

In the first phase of the repairing ablation, the depth of tissue ablated increases linearly in the direction of a vector pointing toward the true optical center 10 of the eye and originating from the center 16 of the misplaced excimer ablation.

Figure 9:
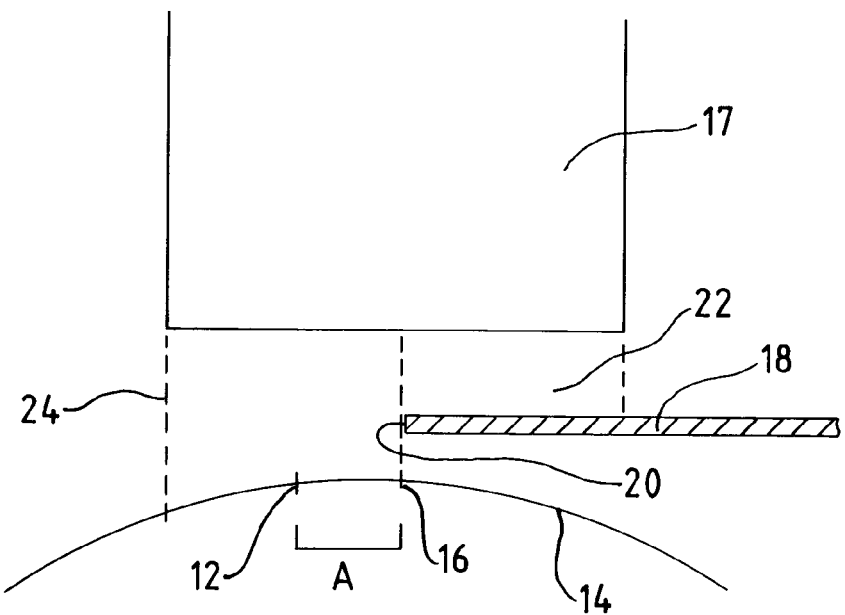
FIG. 9 is a diagrammatic elevational view, showing the apparatus during the first correction phase.
Figure 10:
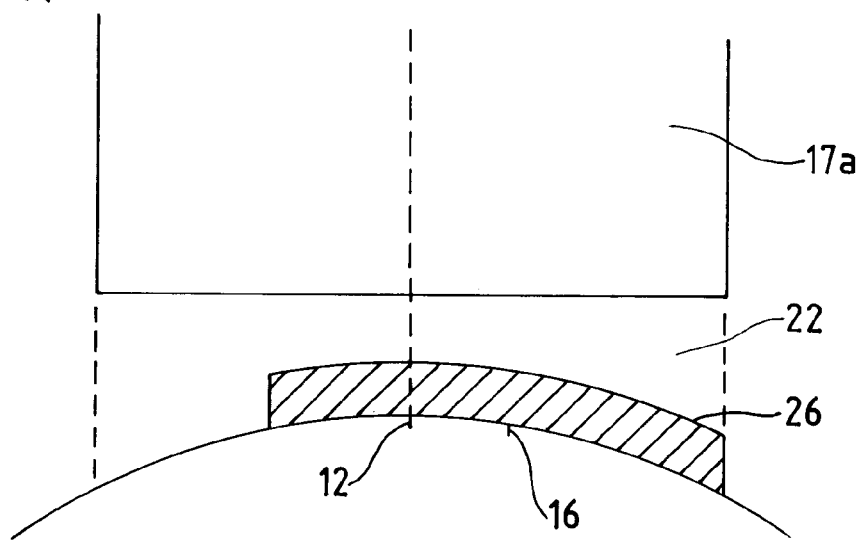
FIG. 10 is a diagrammatic elevational view, showing the apparatus during the second phase of the correction procedure.

Referring to FIGS. 9 and 10, the laser 17 producing the ablation is capable of producing a uniform energy across a circular disc area. This uniform type of ablation pattern is the kind of the kind produced by "broad beam" lasers such as the Summit Apex Plus operating in the phototherapeutic keratectomy (PTK) mode. More recently FDA approved lasers may produce a uniformly increasing ablation by repeated pulsation or spots more in one area than another rather than by physical blockage of a beam. This invention is intended to cover any method to produce a uniformly increasing ablation for repair of off-centered excimer laser ablations.

Referring to FIGS. 2–5 and 9, in one embodiment a device for producing a first phase of the repair ablation comprises a laser masking device 18 in the general form of a straight-edge closing door in the path of the treating beam much like the closing of a garage door. The distance across the cornea that the device 18 moves per repairing laser shot taken would be governable by the operator. The direction of the travel of the laser masking device 18 is movable within a range of 360 degrees and controllable by the operator.

Referring to FIGS. 2–5 and 9, the therapeutic device 18 has a straight edge 20 which closes with a pre-set speed over a pulsing, uniform-energy circular disc-shaped laser beam 22 (FIG. 9). The speed of the moving masking device 18 is governed by the number of phototherapeutic laser shots that the laser 17 fires per second. Thus the device 18 closes at a rate governed by the number of laser pulses fired. With the device 18 moving at a uniform speed, there is a linearly increasing number of laser shots fired at points further and further along the path of the moving device 18.

The operative plan for the direction of increasing excimer ablation is determined by inspection of a subtraction elevation corneal mapping of the operated eye. The rate of increase of the depth of ablated tissue per millimeter along the just mentioned vector is proportional to the product of (a) the number of diopters of myopia treated in the initial excimer ablation, and (b) how far off center was the initial ablation.

Laser masking device 18 moves in such a way that the amount of tissue in microns, Z, ablated at a point along the x axis of device 18 is given by the formula Z=DA×microns, where A is the distance between the true optical center 12 of the eye and the actual center 16 of the misfired laser ablation, D is the dioptic power of the spherical ablation attempted and x is the distance in millimeters along the X-axis, where the X axis is defined by the wrong center 16 of the excimer ablation and the true optical center 12 of the cornea. The distance, A, is the distance off the proper center 12 that the actual laser ablation occurred. The value of A is determined by analysis of a subtraction elevation mapping produced by corneal mapping device such as can be done presently using the PAR or Orbscan devices.

In FIG. 9, 12 is the true optical center of the eye and 16 is the center of the wrongly centered laser ablation. 24 is the edge of the laser beam, which is located at the end of the traverse of the closing door. The value of A is the distance between point 12 and point 16. The axis of the device 18 is preferably rotatable over a full 360 degrees because ablations can be off center in any direction.

In an extreme example, a ten diopter ablation is placed a full millimeter off center. In this case, the laser correction should proceed across the cornea at a rate such that dZ/dx=10 microns per millimeter.

Or, if the tissue is ablated at the rate of one micron per three laser pulses, then the rate of motion of laser masking device 18 is one millimeter per 30 laser pulses.

In theory the number of pulses per millimeter should be given by the formula PULSES/mm=(8/3) D A P, where P is the number of laser pulses that the tissue requires per micron of ablation, D is the dioptric power of the initial spherical ablation, and A is the distance in millimeters that the wrong placed ablation is from the true optical center 12.

In practice, there are some degree of measurement error that comes in determining the precise value of A. The value of A is the subtraction of two vectors that depend on the patient looking at a particular point in two separate measurements and there can be no errors there. Because of the measurement errors, it may be prudent to undercorrect the malcentered ablation and use the formula:

PULSES/mm=D A P

Example 1. A routine example is as follows. A three diopter ablation is misplaced to a point 0.33 millimeters off the true optical center 12. IF the laser pulse energy is such that it takes four laser pulses to ablate one micron of tissue, then the rate of motion of device 18 is four pulses per millimeter. For an ablation of a 6.5 mm region, there would be a total of 26 laser pulses used in the correction of the maltreated region.

Example 2. In a highly myopic patient we might have a ten diopter myopic ablation placed 0.5 millimeters off the true optical center 12. The correcting laser ablation would have device 18 moving so that there are 20 pulses per millimeter being shot as the device moves across the area of the original (wrong) ablation zone to make the repair. For an ablation of 6.5 mm there would be a total of 130 pulses used in the correction of the maltreated region.

Figure 8:
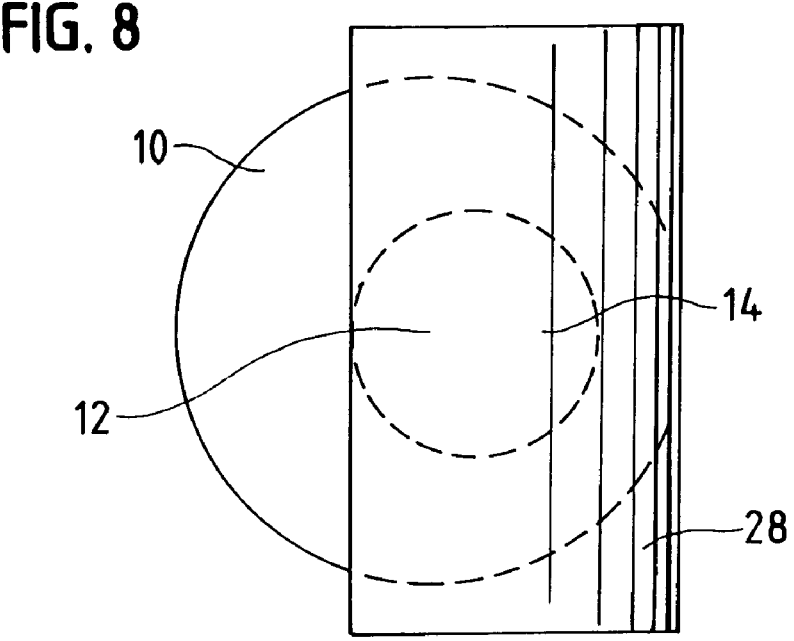
FIG. 8 is a diagrammatic view of the cornea of an eye, with a laser masking device of another embodiment of the invention, diagrammatically shown during the first phase of a correcting method in accordance with the present invention.

In another embodiment of the invention, as illustrated in FIG. 8, instead of using a moving laser masking device 18 during the first phase of the repairing ablation, a stationary laser masking device 28 is placed in front of the laser beam. In order for the energy of the laser to increase in a direction from the offset center 16 toward the correct center 12, laser masking device 28 has a laser energy penetrability that varies from less penetrable to more penetrable in a direction from the offset center 16 toward the correct center 12. In one form, laser masking device 28 is formed of indestructible material such as a laser beam resistive gas in a container whose thickness varies linearly. In another form, the thickness of masking device 28 varies linearly from more thick to less thick in the direction from the offset center 16 to the correct center 12.

Repairing the Rest of the Cornea

In one form of the invention, after the supplemental ablation of the first phase illustrated in FIGS. 2–5 and 9 occurs, the second phase of the repairing ablation is a laser treatment over an area that is centered over the optical center of the cornea. The second phase of the repairing ablation is a laser treatment covering an area of a disc measuring a diameter equal to the diameter of the initial ablation plus twice the distance to which the initial ablation was off center. The ablation repeats the treatment of the number of diopters of myopia that were in the original off-center ablation but now the area of the off-center ablation is covered up by an excimer-laser beam impervious shield. The optical center of the cornea can be found either by the method described above or by marking the center of the off-center ablation and using the vector from the subtraction corneal mapping to point back toward the true optical center.

Figure 6:
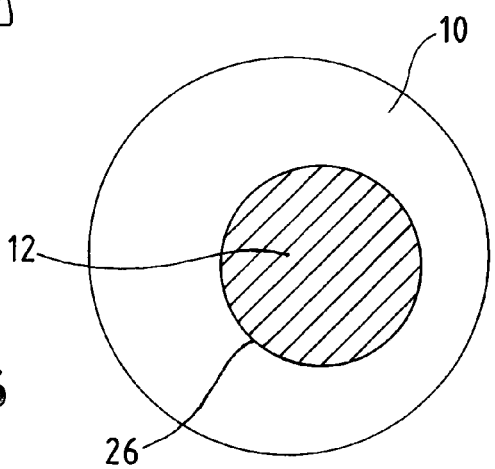
FIG. 6 is a diagrammatic view showing a laser shield in place over the original ablated area during the second phase of the correcting method.
Figure 7:
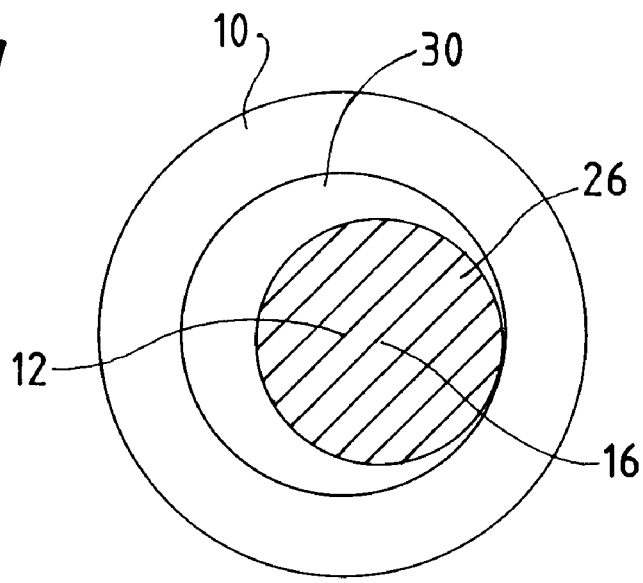
FIG. 7 is a diagrammatic view showing a subsequent laser ablation during the second phase, with the laser shield in place.

The disc area of the second phase of the repairing ablation contains the area of the first phase of the repairing ablation, but the area of the first phase of the repairing ablation is protected from laser treatment. To this end, referring to FIGS. 6 and 10, a laser shield 26 is provided over the supplemental laser ablation after laser 17 is off and device 18 (or device 28) has been removed. Laser 17a is then centered over correct center 12 so that beam 22 will produce an ablation in the location where the ablation should have been produced if correctly centered. With laser shield 26 in place, as illustrated in FIG. 10 another laser ablation will be performed with the energy of an original ablation as if the correction were not occurring. This will produce a crescent-shaped area ablation 30 (FIG. 7). When laser shield 26 is removed, the off center ablation will have been repaired by the new ablation that has resulted from the supplemental laser treatment of the first phase and the additional second phase treatment.

In another form of the invention, instead of using laser shield 26, the computer controlling the laser beam from laser 17a in the second phase is programmed to inhibit laser beam energy from impinging upon the supplemental laser ablation after laser 17 is off and device 18 (or device 28) has been removed. In this manner, the supplemental laser ablation is effectively masked by preventing laser energy from impinging upon the supplemental laser ablation.

In Certain Cases, the Second Phase of the Ablation May Not Be Necessary

I have found that in some cases, such as when the original off-center ablation is offset from true center less than 0.25 mm, the second part of the excimer ablation repair may not be necessary. Such a situation could occur when the original degree of myopia corrected was quite high and even slight ablation malcentrations degrade vision.

It is seen that novel methods and apparatus have been provided for correcting an off-center laser ablation in the cornea. Although illustrative embodiments of the invention have been shown and described, it is to be understood that various modifications and substitutions may be made by those skilled in the art without the departing from the novel spirit and scope of the present invention.

What is claimed is:

1. A method for correcting an off-center laser ablation in the cornea, in which the original ablated area has a center that is offset from the correct optical center of the cornea, comprising the steps of:

determining the correct optical center of the cornea and the offset location of the ablation; and performing a supplemental laser ablation on the cornea with the total energy per area of cornea of the supplemental laser treatment increasing in a direction defined by a vector originating at the offset center and going toward the correct optical center; in which the supplemental laser ablation step includes the step of providing a laser masking device which moves in the direction from the offset center toward the correct optical center, and in which the speed of the masking device is inversely proportional to the product of the distance of the offset center from the correct optical center times the number times the number of diopters of optical correction that were placed in the original ablation.

2. A method as defined in claim 1, including the steps of: introducing a laser shield to cover the entire original ablated area;

performing another laser ablation with the correct optical center as the center of the ablated area and having a new larger ablation radius that covers an area of a disc having a diameter substantially equal to the diameter of the initial ablation plus twice the distance to which the original ablation was off center.

3. A method as defined in claim 1, in which the total energy delivered per area of cornea treated in the supplemental laser treatment increases at a uniform rate.

4. A method as defined in claim 1, in which the masking device moves at a controlled uniform speed.

5. A method as defined in claim 1, in which the supplemental laser ablation uses a pulsing, uniform-energy circular disc-shaped laser beam.

6. A method as defined in claim 1, in which the correct optical center of the cornea is determined by corneal topography.

7. A method as defined in claim 1, in which laser pulses are repeatedly applied to make the total energy applied per area increase substantially linearly in a direction defined by a vector from the offset center toward the correct optical center.

8. A method as defined in claim 1, in which the supplemental laser ablation step includes the step of providing a laser masking device having a laser energy penetrability that varies from less penetrable to more penetrable in a direction from the offset center toward the correct optical center.

9. A method as defined in claim 8, in which the thickness of the masking device varies from more thick to less thick in a direction from the offset center to the correct optical center.

10. A method as defined in claim 1, in which the laser masking device has a straight edge.

11. A method as defined in claim 10, in which the laser masking device moves at a preset speed.

12. A method as defined in claim 11, in which the supplemental laser ablation uses a pulsing, uniform-energy circular disc-shaped laser beam.

13. A method for correcting an off-center laser ablation in the cornea, in which the original ablated area has a center that is offset from the correct optical center of the cornea, comprising the steps of:

determining the correct optical center of the cornea and the offset location of the ablation;

performing a supplemental laser ablation on the cornea with the laser being covering generally the original ablated area, and with the energy of the supplemental laser increasing at a uniform rate in a direction from the offset center toward the correct optical center;

said supplemental laser ablation step including the step of providing a laser masking device which moves in a direction from the offset center toward the correct optical center;

the speed of the masking device being inversely proportional to the product of the distance of the offset center from the correct optical center times the number of diopters of optical correction that were placed in the original ablation; and performing another laser ablation with the correct optical center as the center of the ablated area and having a new larger ablation radius that covers an area of a disc having a diameter substantially equal to the diameter of the initial ablation plus twice the distance to which the original ablation was off center.

14. A method as defined in claim 13, in which the laser masking device has a straight edge.

15. A method as defined in claim 13, in which the supplemental laser ablation uses a pulsing, uniform-energy circular disc-shaped laser beam.

16. A method as defined in claim 15, in which the supplemental laser ablation step includes the step of providing a laser masking device having a laser energy penetrability that varies from less penetrable to more penetrable in a direction from the offset center toward the correct optical center.

17. A method as defined in claim 15, in which the correct optical center of the cornea and the offset location of the ablation are determined by corneal topography elevation subtraction mapping.

18. A method as defined in claim 17, including the step of using a laser for said another laser ablation having a laser beam that is inhibited from impinging upon the original ablated area.

* * * * *